United States Patent [19]

Harvey et al.

[11] 4,444,746
[45] Apr. 24, 1984

[54] VISUALLY CLEAR LAKE COLORED DENTIFRICE

[75] Inventors: Kenneth Harvey, Wilmslow; Harry Hayes, Warrington, both of England

[73] Assignee: Colgate-Palmolive Company, New York, N.Y.

[21] Appl. No.: 444,099

[22] Filed: Nov. 24, 1982

[30] Foreign Application Priority Data

Nov. 24, 1981 [GB] United Kingdom ............... 8135326

[51] Int. Cl.³ .......................... A61K 7/16; A61K 7/18
[52] U.S. Cl. ...................................... 424/49; 424/7.1; 424/52; 424/54
[58] Field of Search .................. 424/49–58, 424/7.1

[56] References Cited

U.S. PATENT DOCUMENTS

| | | | |
|---|---|---|---|
| 3,881,529 | 5/1975 | Mannara | 141/100 |
| 3,919,409 | 11/1975 | Perla et al. | 424/49 |
| 3,928,555 | 12/1975 | Gault | 424/49 |
| 3,928,559 | 12/1975 | Patino | 424/49 |
| 3,929,987 | 12/1975 | Colodney | 424/49 |
| 3,929,988 | 12/1975 | Barth | 424/49 |
| 3,935,306 | 1/1976 | Roberts et al. | 424/49 |
| 3,946,108 | 3/1976 | Tomlinson et al. | 424/49 |
| 3,952,782 | 4/1976 | Mannara | 141/100 |
| 3,955,942 | 5/1976 | Cordon | 424/49 |
| 3,957,964 | 5/1976 | Grimm | 424/49 |
| 3,957,968 | 5/1976 | Cordon | 424/49 |
| 3,980,767 | 9/1976 | Chown et al. | 424/49 |
| 4,002,732 | 1/1977 | Gault | 424/49 |
| 4,003,971 | 1/1977 | Mannara | 424/49 |
| 4,007,259 | 2/1977 | Patino et al. | 424/49 |
| 4,020,154 | 4/1977 | Perla et al. | 424/49 |
| 4,066,745 | 1/1978 | Tomlinson | 424/49 |
| 4,069,311 | 1/1978 | Mannara | 424/49 |
| 4,069,312 | 1/1978 | Mannara | 424/49 |
| 4,071,614 | 1/1978 | Grimm | 424/49 |
| 4,075,316 | 2/1978 | Cordon | 424/49 |
| 4,089,943 | 5/1978 | Roberts et al. | 424/49 |
| 4,098,435 | 7/1978 | Weyn | 222/94 |
| 4,122,976 | 10/1978 | Kenkaire et al. | 222/94 |
| 4,211,341 | 7/1980 | Weyn | 424/49 X |
| 4,223,003 | 9/1980 | Scheller | 424/7.1 |
| 4,240,566 | 12/1980 | Bergman | 206/219 |
| 4,254,894 | 3/1981 | Fetters | 222/1 |
| 4,368,089 | 1/1983 | Smith | 424/49 |
| 4,376,762 | 3/1983 | Hauschild et al. | 424/49 |
| 4,376,763 | 3/1983 | Barth et al. | 424/49 |

*Primary Examiner*—Shep K. Rose
*Attorney, Agent, or Firm*—Robert L. Stone; Murray M. Grill; Herbert S. Sylvester

[57] ABSTRACT

There is disclosed a visually clear colored dentifrice comprising a liquid vehicle having a refractive index between about 1.36 and 1.47, up to about 10% by weight of a gelling agent, about 5–50% by weight of a polishing material having a refractive index similar to that of that of the said liquid vehicle, such that the said dentifrice is visually clear in appearance when the said polishing material is dispersed in the said liquid vehicle and about 0.004–1% by weight of a lake pigment insoluble in water and in the said liquid vehicle, the said lake pigment containing an inherently colorless substrate.

6 Claims, No Drawings

VISUALLY CLEAR LAKE COLORED DENTIFRICE

The present invention relates to visually clear dentifrices.

Visually clear dentifrices have been marketed in recent years in view of their desirable aesthetic aspect combined with their ability to provide desired hygenic and prophylactic effects to teeth and the oral cavity.

In visually clear dentifrices, it is necessary to select insoluble solid components with care since a close match between the refractive index of a solid component and the refractive index of the liquid vehicle is needed in order to provide clarity. For instance, a liquid vehicle mainly of glycerine and/or sorbitol with some water may be proportioned to have a refractive index of about 1.45 and a siliceous polishing material having a similar refractive index incorporated therein.

In order to increase their attractiveness, clear dentifrices have been dyed with water soluble dyes to make them red, yellow, orange, violet, blue, green or other colours. Indeed in British Pat. No. 1,289,323 a plurality of water-soluble dyes are used to make discreetly coloured portions of a clear dentifrice. Insoluble pigment materials have been avoided, since it would have been expected that the match of refractive indices needed for clarity between liquid and solid ingredients would be complicated by the presence of an undissolved, dispersed pigment.

It is an advantage of the present invention that, quite unexpectedly, the insoluble aluminium lake pigments are effective and in fact, provide great stability in colouring visually clear dentifrices. Other advantages will be apparent from consideration of the following disclosure.

In accordance with certain of its aspects, this invention relates to a visually clear coloured dentifrice comprising a liquid vehicle having a refractive index between about 1.36 and 1.47, up to about 10% by weight of a gelling agent, about 5-50% by weight of a polishing material having a refractive index similar to that of that of the said liquid vehicle, such that the said dentifrice is visually clear in appearance to the extent of being transparent or translucent when the said polishing material is dispersed in the said liquid vehicle and about 0.004-1% preferably 0.005 to 0.04 and especially 0.01 to 0.04% by weight of a lake pigment insoluble in water and in the said liquid vehicle, the said lake pigment containing an inherently colourless substrate.

The dentifrice of the present invention contains a liquid vehicle which generally comprises humectant and may include some water. The liquids are selected and if necessary, proportioned to have a refractive index between about 1.36 and 1.47. Refractive indices in this range match refractive indices of dentifrice polishing agents such as sodium aluminosilicates (or silica containing combined alumina), described in British Pat. Nos. 1,348,492 and 1,347,650 silica xerogels, described in British Pat. Nos. 1,186,706 and 1,264,292, insoluble potassium metaphosphate and water-soluble alkali metal phosphates described in British Pat. No. 1,424,034 and synthetic amorphous silica as described in U.S. Pat. Nos. 3,939,262 and 4,007,260.

The most commonly employed humectants for dentifrices are glycerine (refractive index of 1.47) and sorbitol (refractive index of 1.45 in 70% solution). Other humectants such as low molecular weight polyethylene glycols (e.g. having an average molecular weight of about 400) and propylene glycol may also be employed in a liquid vehicle having a proper refractive index.

Water may also form a portion of the liquid vehicle. Its refractive index is 1.33. When a polishing agent having a refractive index of about 1.44–1.47 is used, it may be necessary to limit the amount of free water to up to about 10% by weight of the dentifrice, e.g. about 3–5%; however, when polishing agents of lower refractive index, such as those described in British Pat. No. 1,424,034 and U.S. Pat. No. 3,939,262 and 4,007,260 are used, larger amounts of free water such as about 15% or more may be present. The expression "free water" refers to water which is not specifically associated with sorbitol or another dentifrice component. The liquid vehicle typically comprises at least about 20% by weight of the dentifrice, e.g. about 20–80% preferably about 50–75%.

Polishing agents of the type which have refractive indices which can be closely matched with the refractive index of the liquid vehicle have been indicated above. In general, sodium aluminosilicates and silica xerogels having refractive indices in the range of about 1.44 to 1.47 are employed and the liquid vehicle is proportioned to have a refractive index similar to that of the polishing agent, typically within about 0.01 unit and preferably within about 0.005 unit or less. The polishing agent typically comprises about 5–50% by weight, preferably about 10–30% and most preferably about 15–25%, of the dentifrice.

In addition to the liquid vehicle, the dentifrice contains a solid vehicle portion of a gelling agent, possibly supplemented with a thickener to provide gel character to the dentifrice. Typical gelling agents are natural or synthetic gum or gum-like materials, e.g. Irish moss, gum tragacanth, alkali metal carboxymethyl or carboxyethyl cellulose, hydroxyethyl cellulose, xanthan, polyvinyl pyrrolidone, starch, water-soluble hydrophilic colloidal carboxyvinyl polymers such as those sold under the trade names Carbopol 934 and Carbopol 940 (CARBOPOL is a Trade Mark) and synthetic inorganic silicated clays such as those sold under the trade names Laponite CP and Laponite SP (LAPONITE is a Trade Mark). These grades of Laponite have the formula

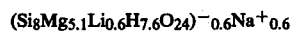

$$(Si_8Mg_{5.1}Li_{0.6}H_{7.6}O_{24})^{-0.6}Na^+_{0.6}$$

The solid portion of the vehicle is typically present in an amount up to 10% by weight of the dentifrice, preferably in the range from 0.5 to 5% by weight. When employed, such grades of Laponite are preferably used in amounts in the range of from 1 to 5% by weight.

Synthetic finely divided silicas such as those sold under the trade names Cab-O-Sil M-5, Syloid 24, Syloid 266, Aerosil D200 and Zeosyl 200 and mixtures thereof may also be employed in amounts of from 0.5 to 20% by weight to promote thickening or gelling and to improve the clarity of the dentifrice.

The lake pigment employed in the dentifrice contains an inherently colourless substrate. Typical desirable substrates are alumina, zirconia, and titania, most preferably alumina. These substrates absorb the pigment onto their surfaces.

The Lakes are familiar to dye chemists. For instance, they are described in the *Handbook of U.S. Colourants for Foods, Drugs, and Cosmetics*, D. M. Marmion, Wiley-Interscience Publication, e.g. at pages 30–31, 96, 106, and 170–172. Many are available from the Anstead Company (U.K.) and are described in this Company's Booklet. They are water-insoluble pigments formed by precipitation and extension of a soluble dye onto an insoluble base or substratum, such as alumina, zirconia, or titania. D & C colours and FD & C colours may be used. Water-soluble dyes colour objects by absorption or attachment from their solution to the material which is coloured; lakes, differently, provide colour by dispersion in the medium which is coloured. The success of lakes in coloured visually clear dentifrices in particularly unexpected since opacity is a general property of lakes.

The following dyes are illustrated with typical appropriate substrata therefor:

| SUBSTRATE | PATENT DYESTUFF | 1971 COLOUR INDEX NUMBER |
|---|---|---|
| Alumina | Ponceau 4R (red) | 16255 |
| | Carmoisine (red) | 14720 |
| | Amaranth (red) | 16185 |
| | Erythrosine (pink) | 45430 |
| | Red 2 G (red) | 18050 |
| | Tartrazine (yellow) | 19140 |
| | Yellow 2G (yellow) | 18965 |
| | Sunset Yellow (orange) | 15985 |
| | Quinoline Yellow (yellow) | 47005 |
| | Green S (green) | 44090 |
| | Indigo Carmine (blue) | 73015 |
| | Patent Blue V (blue) | 42051 |
| | Brilliant Blue FCF | 42090 |
| Titania | D & C Red No. 19 | 45170 |
| | D & C Red No. 21 | 45380 |
| | D & C Red No. 27 | 45410 |
| | D & C Orange No. 5 | 45370 |

Other pigmented lakes which may be used with the various substrata are:

| | 1971 COLOUR INDEX NUMBER |
|---|---|
| FD & C Red No. 2 Lake | 16185 |
| FD & C Red No. 3 Lake | 45430 |
| FD & C Red No. 40 Lake | 16035 |
| FD & C Yellow No. 5 Lake | 19140 |
| FD & C Yellow No. 6 Lake | 15985 |
| FD & C Blue No. 1 Lake | 42090 |
| FD & C Blue No. 2 Lake | 73015 |
| Dispersed Blue (Patent Blue V) Lake | 12726 |
| Dispersed Blue Lake | 18010 |

Typically about 10–40% of the lake is the water-soluble dye.

The preferred lakes are on alumina with dispersed blues C.I. 12726 and 18010 being preferred. The lakes are typically present in an amount of 0.011 to 0.04% e.g. about 0.02%, when the red dyes are used in the alumina lake (depending on the dye content of the lake) and up to about 0.005 to 0.04% when the blue dyes or the green dyes are used in the alumina lake. Lakes of other colours are also used in appropriate amounts (depending on the pure dye content of the lake) to provide desired colour depth.

It is preferred that the lake pigment is present in an amount not in excess of 0.035% by weight.

The quality or depth of the colour may be modified, if desired, by including a water-soluble dye such as those listed above, separate from the lake in the visually clear dentifrice.

The water-soluble dye should complement the colour effect of the lake. For instance, Patent Blue V is desirable when used with an alumina lake such as dispersed Blue 12726 lake. Typically about 5 to 10 times as much lake is used over the amount of separate water-soluble dye.

Organic surface-active agents may be used in the compositions of the present invention to achieve increased prophylactic action, assist in achieving thorough and complete dispersion of the compositions of the present invention throughout the oral cavity, and render the compositions of the present invention more cosmetically acceptable. The organic surface-active material may be anionic, nonionic, ampholytic, or cationic in nature, and it is preferred to employ as the surface-active agent a detersive material which imparts to the composition detersive and foaming properties. Suitable types of such detergents include water-soluble salts of higher fatty acid monoglyceride monosulphates, such as the sodium salt of the monosulphated monoglyceride of hydrogenated coconut oil fatty higher alkyl sulphates, such as sodium lauryl sulphates, sodium $C_{12-18}$ alkyl sulphate, alkyl aryl sulphonates, such as sodium dodecyl benzene sulphonate, olefin sulphonates, such as sodium olefin sulphonate in which the olefin group contains 12–21 carbon atoms, higher alkyl sulphoacetates, higher fatty acid esters of 1,2-dihydroxy propane sulphonates, and the substantially saturated higher aliphatic acyl amides of lower aliphatic amino carboxylic acid compounds, such as those having 12–16 carbons in the fatty acid alkyl or acyl radicals. Examples of the last mentioned amides are N-lauroyl sarcosine, and the sodium, potassium, and ethanolamine salts of N-lauroyl, N-myristoyl or N-palmitoyl sarcosine, which should be substantially free from soap or similar higher fatty acid material which tends to substantially reduce the effect of these compounds. The use of these sarcosine compounds in dentifrice compositions of the present invention is particularly advantageous since these materials exhibit a prolonged and marked effect in the inhibition of acid formation in the oral cavity due to carbohydrate breakdown in addition to exerting some reduction in the solubility of tooth enamel in acid solutions.

Other particularly suitable surface-active materials include nonionic agents such as condensates of sorbitan monostearate with approximately 20 moles of ethylene oxide, condensates of ethylene oxide with propylene oxide, condensates of propylene glycol ("Pluronics") and amphoteric agents such as quaternized imidazole derivatives, which are available under the trademark "Miranol" $C_2M$. Cationic surface active germicides and antibacterial compounds such as diisobutylphenoxyethoxyethyl dimethyl benzyl ammonium chloride, benzyl dimethyl stearyl ammonium chloride, tertiary amines having one fatty alkyl group (of from 12–18 carbon atoms) and two (poly) oxyethylene groups attached to the nitrogen (typically containing a total of from about 2 to 50 ethanoxy groups per molecule) and salts thereof with acids, and compounds of the structure

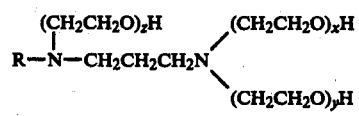

where R represents a fatty alkyl group containing from about 12 to 18 carbon atoms, and x, y and z total 3 or higher, as well as salts thereof with mineral or organic acids, may also be used. It is preferred to use from about 0.05 to 5% by weight of the foregoing surface-active materials in the oral preparation of the present invention.

Any suitable flavouring or sweetening materials may be employed in formulating a flavour for the compositions of the present invention. Examples of suitable flavouring constituents include the flavouring oils, e.g. oils of spearmint, peppermint, wintergreen, sassafras, clove, sage, eucalyptus, marjoram, cinnamon, lemon and orange, as well as methylsalicylate. Suitable sweetening agents include sucrose, lactose, maltose, sorbitol, sodium cyclamate, perillartine and saccharine. Suitably, flavour and sweetening agents may together comprise from about 0.01 to 5% or more of the composition of the present invention. Chloroform may also be used.

The compositions of the present invention may also contain a fluorine-containing compound having a beneficial effect on the care and hygiene of the oral cavity, e.g. diminution of enamel solubility in acid and protection of the teeth against decay which do not substantially detract from the clarity of the dentifrice. Examples thereof include sodium fluoride, potassium fluoride and complex fluorides, particularly sodium monofluorophosphate. These materials, which dissociate or release fluorine-containing ions, suitably may be present in an effective but non-toxic amount, usually within the range of about 0.01 to 1% by weight of the water-soluble fluorine content thereof. Sodium fluoride and sodium monofluorophosphate are particularly preferred as well as mixtures thereof.

Various other materials may be incorporated in the oral preparations of this invention. Examples thereof are colouring or whitening agents or dyestuffs, preservatives, silicones, chlorophyll compounds, ammoniated materials such as urea, diammoniumphosphate and mixtures thereof, and other constituents. The adjuvants are incorporated in the compositions of the present invention in amounts which do not substantially adversely affect the properties and characteristics desired and are selected and used in proper amounts depending upon the particular type of preparation involved.

Antibacterial agents may also be employed in the oral preparations of the present invention in an amount of about 0.01-5% by weight. Typical antibacterial agents include $N^1$-(4-chlorobenzyl)-$N^5$-(2,4-dichlorobenzyl biguanide;
p-chlorophenyl biguanide;
4-chlorobenzhydryl biguanide;
4-chlorobenzhydrylguanylurea;
N-3-lauroxypropyl-$N^5$-p-chlorobenzylbiguanide;
1,6-di-p-chlorophenylbiguanidohexane;
1,6-bis(2-ethylhexylbiguanido) hexane;
1-(lauryldimethylammonium)-8-(p-chlorobenzyldimethylammonium) octane dichloride;
5,6-dichloro-2-guanidinobenzimidazole;
$N^1$-p-chlorophenyl-$N^5$-laurylbiguanide;
5-amino-1,3-bis(2-ethylhexyl)-5-methylhexahydro pyrimidine;
and their non-toxic acid addition salts.

In the manufacture of dentifrices, it is conventional to remove entrained air from the product by deaeration under vacuum typically at a late stage in the manufacture. If desired the dispersed, immobile air bubbles desirably can be permitted to remain as they can enhance the appearance of the dentifrice. Furthermore, air can be at least partially removed and reintroduced as substantially globular or spheroidal bubbles of say about 0.1-8 mm, preferably about 0.5-5 mm in size, well distributed in the gel at an average of at least one per cubic centimeter. Such air bubbles may be placed in the gel by stirring it while introducing air. Instead of air, bubbles of another gas, such as nitrogen or carbon dioxide, can be introduced in non-toxic quantity. In particular, carbon dioxide can provide an effervescent character to the dentifrice.

In the event it is desired to have a minimum amount of air in the dentifrice of the present invention, the "Unimix" apparatus described in "Process Engineering" Sept. 11, 1970, pages 81-85, is particularly efficacious for this purpose. In this apparatus a mixing tool can be rotated in clockwise or counterclockwise manner, and the action of the mixing tool is followed by the action of a scraper blade to ensure that the working surface of the apparatus is scraped clean. Preferably, a plastic such as polytetrafluorethylene is used as the scraper since it is compatible with the various ingredients of the dentifrice. The positioning of the mixing tool and the scraper from a raised central column in the apparatus and the further presence of a hydraulically operated vacuum tight lid permits but little air to enter the formulation during processing. Thus, gelling agent and a portion of liquid including water and/or humectant can be efficiently blended in the Unimix apparatus. Then the remaining liquid can be separately blended with the polishing agent and additional components (except for post-added components, such as flavouring oil) in the Unimix, and then the two dispersions blended together in the Unimix apparatus. If desired, the small amount of air can be largely removed under the depressurized conditions in the apparatus. The apparatus can be used to blend ingredients at room temperature as well as at higher temperatures.

Furthermore, if desired, visible particles of dyes, pearlescent flakes or particles of insoluble salts of antibacterial agents such as the monofluorophosphate salt or the disarcosinate salt of 1,6-di-p-chlorophenylbiguanidoxhexane, as well as other particles, can be distributed in the dentifrice.

The dentifrices should have a pH practicable for use. A slightly acid to slightly alkaline pH is preferred. The dentifrices may be packaged in lined or unlined aluminium tubes, lined lead tubes, plastic tubes or aerosol or pump tubes.

The invention may be put into practice in various ways and a number of specific embodiments will be described to illustrate the invention with reference to the accompanying Examples. All amounts are by weight unless otherwise indicated.

EXAMPLES 1 TO 4

Visually clear dentifrices were prepared and deaerated. The dentifrices had the following compositions:

| | Example | | | |
|---|---|---|---|---|
| | 1A | 2A | 3A | 4A |
| INGREDIENTS | | PARTS | | |
| Glycerine | 25.000 | 25.000 | 25.000 | 25.000 |
| Sorbitol (70% aqueous soln.) | 44.053 | 44.484 | 45.984 | 44.405 |
| Sodium Saccharine | 0.170 | 0.170 | 0.170 | 0.170 |
| Sodium Carboxymethyl Cellulose | 0.240 | 0.190 | 0.190 | 0.190 |
| Dispersed Blue Alumina Lake (C.I. 12726) | 0.011 | 0.011 | 0.011 | — |
| Water-soluble FD & C Blue Dye | — | — | — | 0.190 |

|  | Example | | | |
|---|---|---|---|---|
| INGREDIENTS | 1A | 2A | 3A | 4A |
|  | PARTS | | | |
| Blue Dye (1%) | | | | |
| Sodium Fluoride | 0.100 | 0.100 | 0.100 | 0.100 |
| Disodium Monofluoro-phosphate | 0.760 | 0.760 | 0.760 | 0.760 |
| ZeO 49 (ex Huber) Sodium Aluminosilicate (Silica with combined Alumina) | 17.000 | 17.000 | 17.000 | 17.000 |
| Zeosyl 200 (Silica Thickener) | 7.000 | 6.500 | 5.000 | 6.500 |
| Sodium $C_{12-18}$ Alkyl Sulphate | 1.666 | 1.765 | 1.765 | 1.765 |
| Flavour | 1.000 | 1.000 | 1.000 | 1.000 |
| Water | 3.000 | 3.000 | 3.000 | 3.000 |

The blue colour of the visually clear dentifrices of Examples 1 to 3 remained stable longer upon storage than did the blue colour of the visually clear dentifrice of Example 4 which was less deep and faded during storage.

EXAMPLES 2B AND 2C

The colour of the visually clear dentifrice of Example 2 was modified by varying the amount of lake to 0.008 parts (Example 2B) and 0.013 parts (Example 2C), respectively, with corresponding adjustments of the amounts of Sorbitol (70%).

EXAMPLES 5 TO 7

Green lakes were used in amounts comparable to the blue lakes of Examples 1 to 3 with desirable colour and stability.

EXAMPLE 8

Red lakes were used in amounts approximately 3 times greater than the amount of blue lake in Example 2 (approx. 0.033) with desirable colour and stability.

EXAMPLES 9 TO 12

Visually clear dentifrices were prepared and deaerated. The dentifrices had the following compositions:

|  | Example | | | |
|---|---|---|---|---|
| INGREDIENTS | 9 | 10 | 11 | 12 |
|  | PARTS | | | |
| Glycerine | 25.0000 | 25.0000 | 25.0000 | 25.0000 |
| Sorbitol (70% aqueous soln.) | 44.5910 | 44.5870 | 44.5790 | 44.4050 |
| Sodium Saccharine | 0.1700 | 0.1700 | 0.1700 | 0.1700 |
| Sodium Carboxymethyl Cellulose | 0.1900 | 0.1900 | 0.1900 | 0.1900 |
| Dispersed Blue Aluminum Lake (C.I. 12726) | 0.0035 | 0.0070 | 0.0140 | — |
| Ultramarine Blue pigment | 0.005 | 0.0010 | 0.0020 | — |
| Water-Soluble FD & C Blue No. 1 (1%) | — | — | — | 0.1900 |
| Sodium Monofluorophosphate | 0.7600 | 0.7600 | 0.7600 | 0.7600 |
| Zeo 49 (ex. Huber) Sodium Aluminosilicate (Silica with combined Alumina) | 17.0000 | 17.0000 | 17.0000 | 17.0000 |
| Zeosyl 200 (Silica Thickener) | 6.5000 | 6.5000 | 6.5000 | 6.5000 |
| Sodium $C_{12-18}$ Alkyl Sulphate | 1.7650 | 1.7650 | 1.7650 | 1.7650 |
| Flavour | 1.0000 | 1.0000 | 1.0000 | 1.0000 |
| Water | 3.0000 | 3.0000 | 3.0000 | 3.0000 |

The blue colour of the visually clear dentifrices of Examples 9 to 11 remained stable longer upon storage than did the blue colour of the visually clear dentifrice of Example 12, which was less deep and faded during storage.

We claim:

1. A visually clear lake colored dentifrice comprising a liquid vehicle having a refractive index between about 1.36 and 1.47, up to about 10% by weight of a gelling agent, about 5–50% by weight of a polishing material having a refractive index similar to that of that of the said liquid vehicle, such that the said dentifrice is visually clear in appearance when the said polishing material is dispersed in the said liquid vehicle and about 0.004–1% by weight of a lake pigment insoluble in water and in the said liquid vehicle, the said lake pigment containing an inherently colorless insoluble base or substrate comprising alumina, zirconia, titania or a mixture thereof having precipitated and extended thereon 10–40% of a water-soluble D & C or FD & C color dye, said lake essentially providing the color to said visually clear dentifrice by dispersion throughout the dentifrice medium which is thereby colored and without dissolution of said water-soluble dye, said color imparted by the insoluble lake pigment remaining stable longer upon storage of said dentifrice than color imparted by water-soluble dye.

2. A dentifrice as claimed in claim 1 in which the said lake pigment has dispersed in it a blue dye and the said lake pigment is present in amount of about 0.005–0.04% by weight.

3. A dentifrice as claimed in claim 3 in which the said lake pigment is Dispersed Blue Colour Index 12726.

4. A dentifrice as claimed in claim 1 in which a red dye is dispersed in the said lake pigment and the said lake pigment is present in amount of about 0.01–0.04% by weight.

5. A dentifrice as claimed in claim 6 in which the lake pigment is present in an amount not in excess of 0.035% by weight.

6. A dentifrice as claimed in claim 1 in which a green dye is dispersed in the said lake pigment and the said lake pigment is present in amount of about 0.005–0.04% by weight.

* * * * *